(12) United States Patent
Klein et al.

(10) Patent No.: US 8,833,138 B2
(45) Date of Patent: Sep. 16, 2014

(54) METHOD AND APPARATUS FOR EVALUATING DYNAMIC FORCES

(75) Inventors: Jake Edward Klein, Tucson, AZ (US); Ronald Robert Madsen, Vail, AZ (US)

(73) Assignee: Texas Instruments Incorporated, Dallas, TX (US)

( * ) Notice: Subject to any disclaimer, the term of this patent is extended or adjusted under 35 U.S.C. 154(b) by 265 days.

(21) Appl. No.: 13/288,600

(22) Filed: Nov. 3, 2011

(65) Prior Publication Data
US 2013/0111973 A1 May 9, 2013

(51) Int. Cl.
| | |
|---|---|
| G01M 7/00 | (2006.01) |
| G01N 3/00 | (2006.01) |
| G01N 33/00 | (2006.01) |
| G01P 15/00 | (2006.01) |
| H01L 21/66 | (2006.01) |
| G01N 3/303 | (2006.01) |

(52) U.S. Cl.
CPC .............. *G01N 3/303* (2013.01); *H01L 22/12* (2013.01)
USPC ...................................................... 73/12.13

(58) Field of Classification Search
USPC .............................................. 73/12.13, 12.6
See application file for complete search history.

(56) References Cited

U.S. PATENT DOCUMENTS

| | | | | | |
|---|---|---|---|---|---|
| 3,266,289 | A * | 8/1966 | Stamy | .......................... | 73/12.13 |
| 3,535,912 | A * | 10/1970 | Muller | ......................... | 73/12.06 |
| 3,693,421 | A * | 9/1972 | Karper et al. | .................... | 73/843 |
| 4,085,609 | A * | 4/1978 | Kelly | ............................... | 73/844 |
| 4,699,000 | A * | 10/1987 | Lashmore et al. | ................ | 73/81 |
| 4,987,766 | A * | 1/1991 | Brar et al. | ..................... | 73/12.13 |
| 5,457,984 | A * | 10/1995 | Ambur et al. | ................ | 73/12.09 |
| 6,389,876 | B1 * | 5/2002 | Tanimura et al. | ............ | 73/12.01 |
| 6,848,293 | B2 * | 2/2005 | DeRuiter et al. | ............. | 73/12.13 |
| 7,287,420 | B2 * | 10/2007 | Yang et al. | ......................... | 73/81 |
| 7,373,802 | B2 * | 5/2008 | Powers et al. | ................ | 73/12.09 |
| 7,628,065 | B2 * | 12/2009 | Yang et al. | .................. | 73/150 A |
| 7,900,499 | B2 * | 3/2011 | Zhang | .......................... | 73/12.13 |
| 8,006,539 | B2 * | 8/2011 | Eggenspieler et al. | ...... | 73/12.11 |
| 2002/0053232 | A1 * | 5/2002 | Axe et al. | ...................... | 73/12.04 |
| 2002/0116090 | A1 * | 8/2002 | Fischer | .......................... | 700/245 |
| 2004/0035181 | A1 * | 2/2004 | DeRuiter et al. | ............. | 73/12.06 |
| 2005/0016256 | A1 * | 1/2005 | Ishikawa | ...................... | 73/12.13 |
| 2005/0082340 | A1 * | 4/2005 | Wiedemann et al. | ......... | 228/103 |
| 2007/0125152 | A1 * | 6/2007 | Brankov | ....................... | 73/12.01 |
| 2007/0269986 | A1 * | 11/2007 | Kalenian et al. | .............. | 438/692 |
| 2008/0110237 | A1 * | 5/2008 | McNamara et al. | ......... | 73/12.13 |
| 2008/0188985 | A1 * | 8/2008 | Sakano | .......................... | 700/260 |
| 2009/0145196 | A1 * | 6/2009 | Kawazoe et al. | .............. | 73/1.89 |
| 2011/0120210 | A1 * | 5/2011 | Saitoh et al. | ................. | 73/12.06 |
| 2011/0314894 | A1 * | 12/2011 | Nie et al. | ..................... | 73/12.09 |

* cited by examiner

*Primary Examiner* — Lisa Caputo
*Assistant Examiner* — Philip Cotey
(74) *Attorney, Agent, or Firm* — Steven A. Shaw; Frederick J. Telecky, Jr.

(57) ABSTRACT

In a method and apparatus for determining the level of dynamic force required to cause damage to an electronic device, the electronic device may be placed beneath a ram assembly of a dynamic impact testing device. Thereafter, the ram assembly may be used to impact the electronic device to determine a threshold level of dynamic force that will cause damage to the electronic device. The ram assembly may then be used to impact a load cell with the threshold level of dynamic force so that the load cell generates a data output.

14 Claims, 10 Drawing Sheets

METHOD AND APPARATUS FOR EVALUATING DYNAMIC FORCES

BACKGROUND

Pick and place machines (sometimes referred to as "PNP" machines) are commonly used during the manufacture of integrated circuit devices. Examples of integrated circuit devices that are commonly handled by pick and place machines during manufacture include Wafer Chip Scale Packages (sometimes referenced simply as "WCSP") and plastic encapsulated integrated circuits.

In operation, a typical pick and place machine will pick up a part (e.g., an integrated circuit device or component thereof) and then place the part in a different relative location. To pick up a part, a contact mechanism, e.g., a vacuum tip, is first moved into contact with the part. If this contact is too forceful, it can damage the part. Such damage usually takes the form of small cracks on the silicon die which may later enlarge during heat cycling (e.g., soldering operations) and cause failure of the integrated circuit device. Similar impact damage can also occur during the pick and place machine placing operation. This internal damage may be completely invisible even with a careful microscopic visual inspection of the part.

Different integrated circuit devices exhibit different sensitivities to impact damage depending, for example, on the thickness of the device or component involved and other factors. As integrated circuit devices trend toward smaller and thinner packages, however, the problem of impact damage is seen to be increasing. Further, as manufacturing processes become faster, the opportunity for impact damage increases.

DETAILED DESCRIPTION

Figure 14:
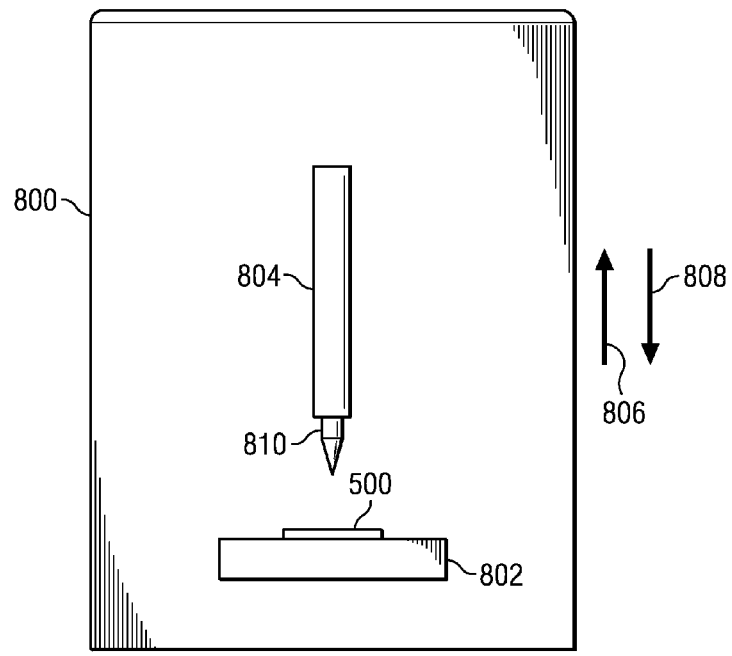
FIG. 14 is a schematic front elevation view of a portion of an exemplary production machine having an integrated circuit device inserted therein.

FIG. 14 schematically illustrates a production machine 800 which may be used in conjunction with the manufacture of an integrated circuit device 500. Production machine 800 performs functions known in the industry as "pick and place" (sometimes referred to simply as "PNP") operations and may, for example, be an STI AT268, STI Sort Maxx TR2016 or an Ismeca NT16 machine.

With further reference to FIG. 14, production machine 800 may include a work platform 802 for supporting an integrated circuit device 500, as shown. Work platform 802 may, for example, be a portion of a conventional rotary table mechanism. A plunger 804 may be reciprocally movable in the upward 806 and downward 808 directions relative to the work platform 802. A tip 810 may be attached to the plunger 804. Integrated circuit device 500 may be any type of integrated circuit device, for example a Wafer Chip Scale Package or a plastic encapsulated integrated circuit.

In operation, the production machine 800 may perform various operations with respect to the integrated circuit device 500. As discussed previously, typical pick and place machines may, for example, use a contact mechanism, e.g., a vacuum tip (such as the vacuum tip 810 shown in FIG. 14) to pick up a part (e.g., the integrated circuit device 500 of FIG. 14) and then place the part in a different location.

In order to pick up the integrated circuit device 500 in the exemplary machine 800 of FIG. 14, for example, the plunger 804 is first moved downwardly in the direction 808, bringing the tip 810 into contact with the integrated circuit device 500. Vacuum is then supplied through the tip 810 such that the integrated circuit device 500 is lifted with the tip when the plunger is moved in the upward direction 806.

It is possible for the initial contact, or impact, between the tip 810 and the integrated circuit device 500 to cause damage to the integrated circuit device. As noted previously, such damage usually takes the form of small internal silicon die cracks which may later enlarge during heat cycling (e.g., soldering operations) and cause failure of the integrated circuit device. Similar impact damage can also occur during the pick and place machine placing operation.

Various machine parameters affect the likelihood of damage being inflicted. One such parameter is the speed at which the plunger 804 moves in the downward direction 806. Another is the "overdrive" setting of the plunger, i.e., the distance the plunger 804 can travel beyond initial contact with the integrated circuit device.

As noted previously, different integrated circuit devices exhibit different sensitivities to impact damage depending, for example, on the thickness of the device or component involved and other factors. Although machine parameters can be adjusted to reduce the likelihood of damage being inflicted to an integrated circuit device, heretofore there has been no way to effectively quantify the amount of impact force required to inflict damage on a particular integrated circuit device. It is important to remember that the damage may be completely invisible on the surface of the integrated circuit device. The damage may be internal to the device and cannot be effectively seen, even with special illumination or magnification. Accordingly, it would be desirable to effectively quantify the amount of impact force that will cause damage to a particular integrated circuit device. It would further be desirable to quantify the amount of impact that can be generated by various pick and place machines under different operating conditions.

It has been found that existing tools that measure force are static in nature and do not allow a dynamic component. The use of such static force measurement devices results in significant errors when attempting to predict die cracks in small dimension packages. A dynamic impact testing device that addresses these limitations is described below.

Figure 1:
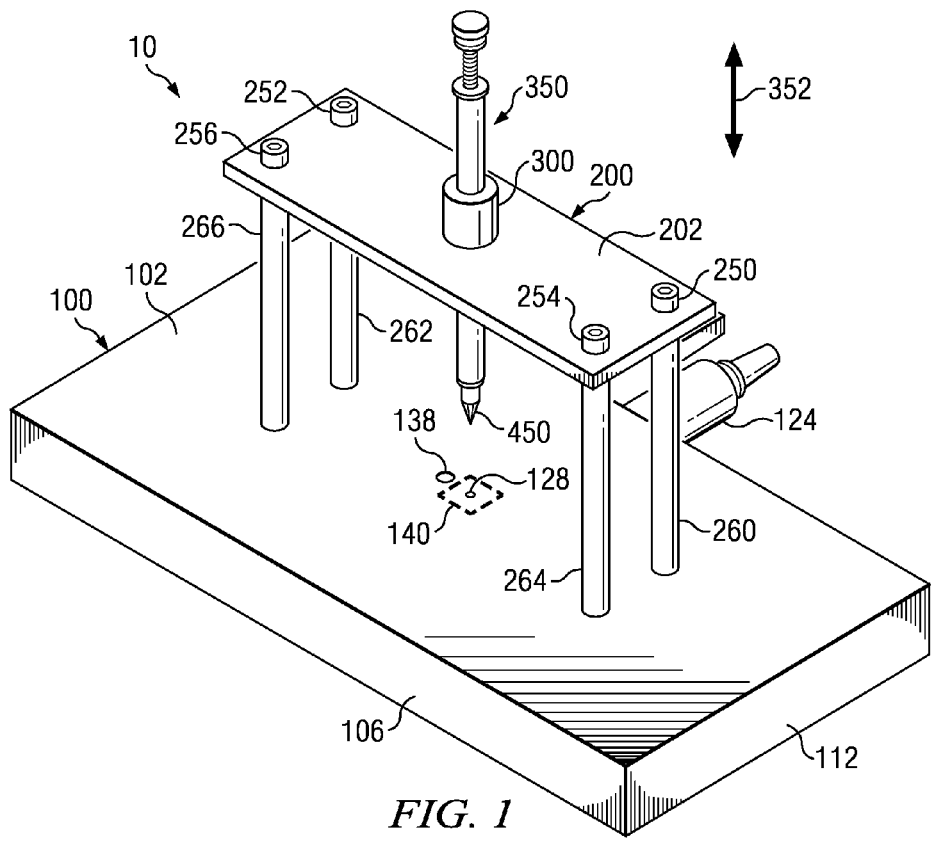
FIG. 1 is a front perspective view of an exemplary embodiment of a dynamic impact testing device.

FIGS. 1-9 show an exemplary embodiment of a dynamic impact testing device 10. As will be explained in further detail herein, the dynamic impact testing device 10 allows for the reproducible application and measurement of various dynamic forces to multiple integrated circuit devices in a laboratory environment. With reference to FIG. 1, dynamic impact testing device 10 may generally include a base portion 100 and a top plate 200 spaced therefrom.

Figure 2:
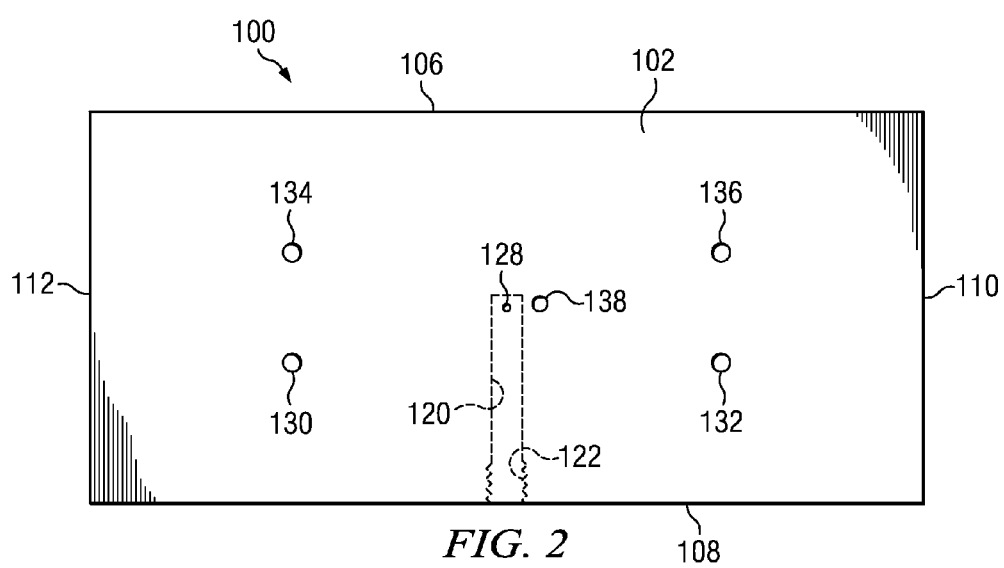
FIG. 2 is a top plan view of a base portion of the exemplary dynamic impact testing device of FIG. 1.
Figure 3:
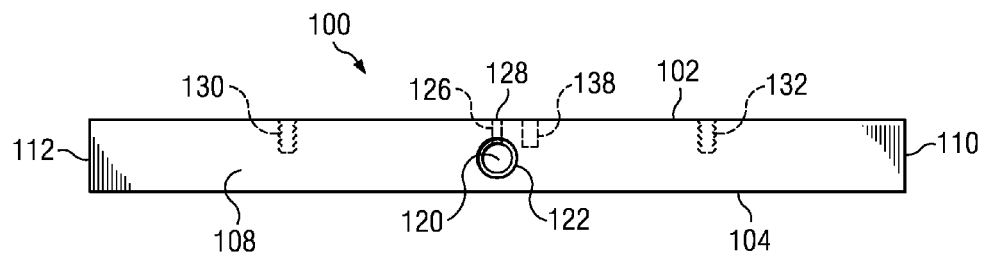
FIG. 3 is a rear elevation view of the base portion of FIG. 2.

FIGS. 2 and 3 illustrate the base portion 100 in further detail. With reference to FIGS. 1-3, base portion 100 may be a one-piece parallelepiped-shaped structure formed, for example, from cold rolled steel. With reference, for example, to FIGS. 2 and 3, base portion 100 may include an upper surface 102 and a spaced parallel lower surface 104. A plurality of vertical surfaces may extend between the upper surface 102 and lower surface 104. These vertical surfaces include a front surface 106, a parallel rear surface 108, and a pair of parallel side surfaces 110, 112.

With further reference to FIGS. 2 and 3, it can be seen that a circular borehole 120 may extend into the base portion 100 from the rear surface 108, as shown. The borehole 120 may include a threaded portion 122 near the rear surface 108 to facilitate threaded attachment of a pneumatic valve assembly 124. FIG. 1. A small borehole 126. FIG. 3, may extend between the borehole 120 and a port 128 formed in the top surface 102 of the base portion 100.

With continued reference to FIGS. 2 and 3, a plurality of threaded holes 130, 132, 134, 136 may be formed in the base portion 100, extending downwardly from the upper surface 102, as shown. As shown in FIGS. 1-3, a non-threaded hole 138 may also extend downwardly from the upper surface 102 into the base portion 100.

Figure 4:
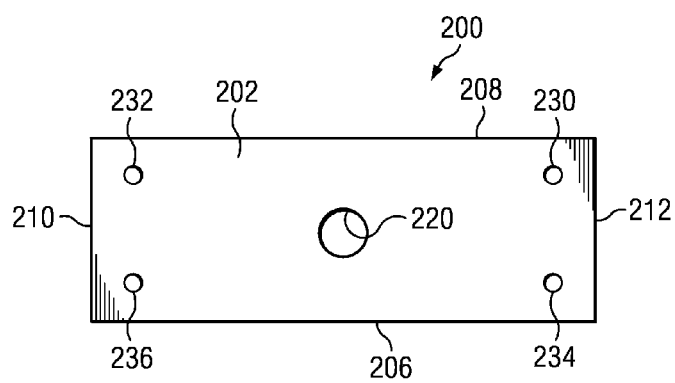
FIG. 4 is a top plan view of a top plate of the exemplary dynamic impact testing device of FIG. 1.

FIG. 4 illustrates the top plate 200 in further detail. With reference now to FIG. 4, top plate 200 may be a one-piece parallelepiped-shaped structure formed, for example, from cold rolled steel. Top plate 200 may include an upper surface 202 and a spaced parallel lower surface, not shown. A plurality of vertical surfaces may extend between the upper surface 202 and the lower surface. These vertical surfaces include a front surface 206, a parallel rear surface 208 and a pair of parallel side surfaces 210, 212.

With further reference to FIG. 4, it can be seen that a centrally located circular hole 220 may be formed in the top plate 200, extending from the upper surface 202 to the oppositely disposed lower surface. A plurality of circular holes 230, 232, 234, 236 may also be formed in the top plate 200, each extending from the upper surface 202 to the oppositely disposed lower surface of the top plate 200, as shown.

With reference to FIG. 1, the top plate 200 may be attached to the base portion 100 via a plurality of threaded screws 250, 252, 254, 256 which may, for example, be stainless steel socket cap screws. Specifically, the screws 250, 252, 254, and 256 may extend through the top plate holes 230, 232, 234, and 236, respectively (FIG. 4), and then through a plurality of un-threaded spacers 260, 262, 264, and 266, respectively (FIG. 1), before threadingly engaging within the bottom portion threaded holes 130, 132, 134, 136, respectively (FIG. 2).

Figure 5:
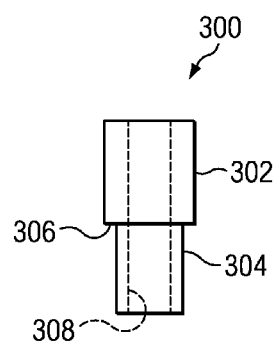
FIG. 5 is a front elevation view of a ram guide member of the exemplary dynamic impact testing device of FIG. 1.

FIG. 5 illustrates a ram guide 300 that may be attached to the top plate 200 in a manner that will be described in further detail herein. With reference now to FIG. 5, ram guide 300 may be generally cylindrical in shape and may, for example, be formed of stainless steel. Ram guide 300 may have a relatively larger diameter upper portion 302 and a relatively smaller diameter lower portion 304. The outside diameter of the lower portion 304 may be substantially equal to the diameter of the circular hole 220 formed in the top plate 200, FIG. 4. With continued reference to FIG. 5, a downwardly facing annular shoulder 306 may be formed at the location where the upper portion 302 and lower portion 304 meet. A hole 308 may extend through the ram guide 300, as shown.

With reference to FIG. 1, the ram guide 300 may be assembled to the top plate 200 by inserting the smaller diameter portion 304 (FIG. 5) of the ram guide 300 into the circular hole 220 (FIG. 4) of the top plate until the ram guide downwardly facing shoulder 306 (FIG. 5) contacts the upper surface 202 of the top plate 200. The ram guide 300 may, for example, be secured in place within the top plate hole 220 using an epoxy adhesive. Alternatively, the ram guide 300 may be secured in place using any conventional mechanism.

With further reference to FIG. 1, a ram assembly 350 may be slidably housed within the ram guide 300, as shown. Specifically, the outside diameter of the ram assembly 350 may slightly smaller than the diameter of the ram guide hole 308 (FIG. 5) such that the ram assembly is free to move in the directions indicated by the arrows 352 (FIG. 1), relative to the top plate 200.

Figure 6:
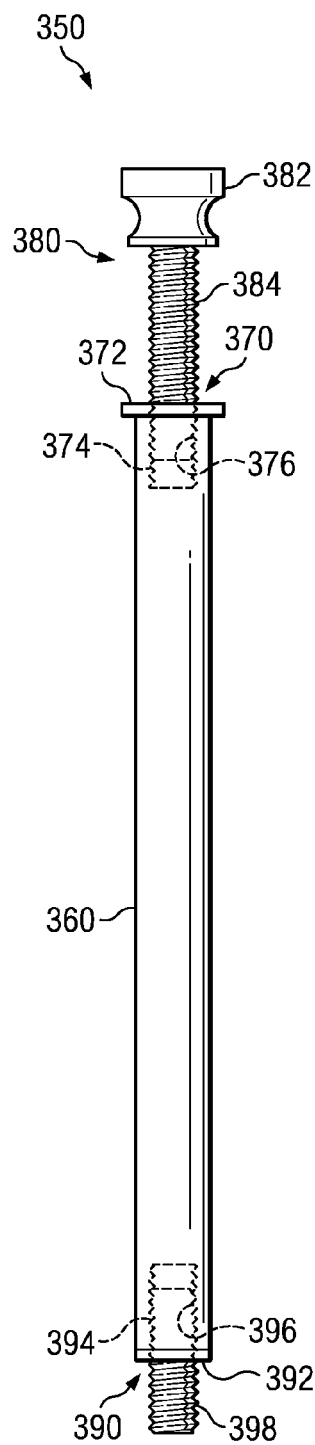
FIG. 6 is a front elevation view of a ram assembly of the exemplary dynamic impact testing device of FIG. 1.

FIG. 6 illustrates the ram assembly 350 in further detail. With reference now to FIG. 6, the ram assembly may include a ram shaft 360 that may, for example, be formed as a hollow carbon fiber tube. A weight support insert 370 may be provided at the upper end of the ram shaft 360, as shown. The weight support insert 370 may include an enlarged diameter shoulder portion 372 and a smaller diameter portion 374 depending therefrom. The smaller diameter portion 374 may be received within the hollow bore of the ram shaft 360 and may, for example, be glued in place in order to securely fasten the weight support insert 370 to the ram shaft 360. A threaded bore 376 may extend through both the shoulder portion 372 and the smaller diameter portion 374 of the weight support insert 370. A thumb screw 380 may include a head portion 382 and a threaded rod portion 384 adapted to be threadingly received within the threaded bore 376 of the weight support insert 370, as shown. The head portion 382 and the threaded rod portion 384 of the thumb screw 380 may, for example, be integrally formed from a plastic material, such as nylon. The weight support insert 370 may, for example, be formed from aluminum.

With continued reference to FIG. 6, a ram tip insert 390 may be provided at the lower end of the ram shaft 360, as shown. The ram tip insert 390 may include an enlarged diameter shoulder portion 392 and a smaller diameter portion 394 depending therefrom. The smaller diameter portion 394 may be received within the hollow bore of the ram shaft 360 and may, for example, be glued in place in order to securely fasten the ram tip insert 390 to the ram shaft 360. A threaded bore 396 may extend through both the shoulder portion 392 and the smaller diameter portion 394 of the ram tip insert 390. A threaded stud 398 may be threadingly received within the threaded bore 396 of the ram tip insert 390, as shown. The threaded stud 398 may, for example, be formed from stainless steel. The ram tip insert 390 may, for example, be formed from aluminum.

Figure 7:
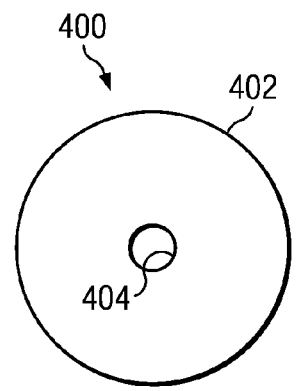
FIG. 7 is a top plan view of an exemplary weight usable in conjunction with the exemplary dynamic impact testing device of FIG. 1.
Figure 8:
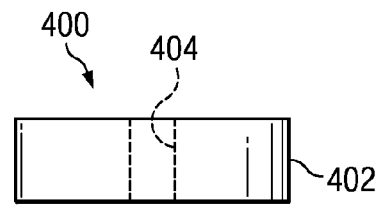
FIG. 8 is a front elevation view of the exemplary weight of FIG. 7.

FIGS. 7 and 8 illustrate an exemplary weight 400 that may be used in conjunction with the dynamic impact testing device 10. With reference to FIGS. 7 and 8, the weight 400 may include a generally cylindrical body portion 402 having a hole 404 formed therein. The weight 400 may, for example, have a mass of about 75 grams.

Figure 9:
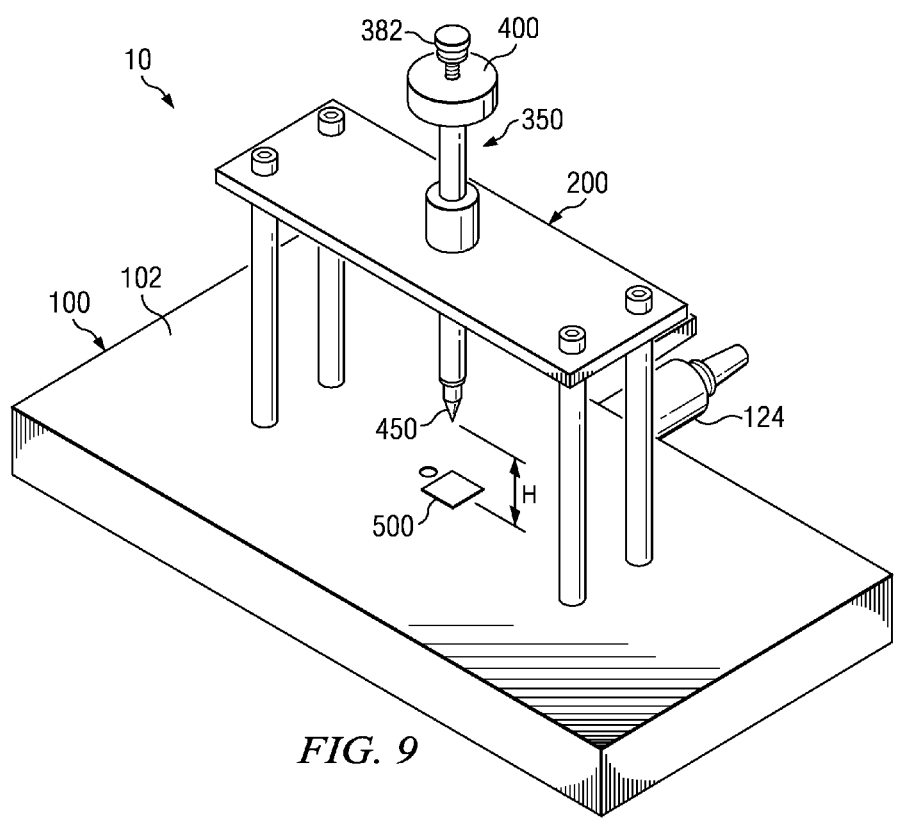
FIG. 9 is a front perspective view of the exemplary dynamic impact testing device of FIG. 1, having an integrated circuit device inserted therein.

In use, the weight 400 may be selectively attached to the ram assembly 350, FIG. 6, in order to vary the weight of the ram assembly. Specifically, with reference to FIG. 6, in order to attach the weight 400 to the ram assembly 350, the ram assembly thumb screw 380 may first be removed from the ram shaft 360 by unscrewing the threaded rod portion 384 of the thumb screw 380 from the threaded bore 376 of the ram assembly weight support insert 370. The thumb screw threaded rod portion 384 may then be inserted through the hole 404 in the weight 400 (FIGS. 7-8), and then threadingly re-engaged with the ram assembly weight support insert threaded bore 376. In this manner, the weight 400 may be secured in place on the ram assembly 350 between the shoulder portion 372 and the head portion 382, in a manner as generally illustrated in FIG. 9.

It is noted that, for the purposes of illustrative clarity, only a single weight 400 having a single mass (e.g., 75 grams) has been shown and described. It is to be understood, however that a plurality of weights, each having a different mass, may be provided in order that different weights and combinations of weights may readily be used to achieve a wide variety of masses that may be added to the ram assembly 350. For example, weights having masses of 0.5 gram, 1 gram, 5 grams, 10 grams, 50 grams, and 100 grams (in addition to the 75 gram weight already described) may be provided in order that a large variety of overall masses may be added to the ram assembly 350, as desired.

With reference to FIG. 1, the ram assembly 350 may further be provided at its lower end with a tip 450. The tip 450 may be attached to the ram assembly 350, for example, by threadingly engaging the tip 450 with the threaded stud 398 of the ram assembly 350, FIG. 6. As can be appreciated, provision of the threaded stud 398 on the ram assembly 350 readily allows various tips to be quickly and easily installed on the ram assembly 350. Further, the design of the ram assembly 350 is such that actual tips from production machines (e.g., the tip 810 in FIG. 14) may be used in order to more closely model the actual production environment dynamic forces during testing.

As can be appreciated with reference to FIG. 1, when the various components of the dynamic impact testing device 10 assembled as described above, ram assembly 350 will be movable in the directions indicated by the arrow 352, directly above a target area 140 defined on the top surface 102 of the base portion 100. The target area 140 may generally surround the port 128 and is located such that the tip 450 of the ram assembly 350, when dropped, will impact approximately at its center.

As mentioned previously, the dynamic impact testing device 10 may be used to reproducibly apply and measure various dynamic forces to multiple integrated circuit devices in a laboratory environment. An exemplary process will now be described wherein the dynamic impact testing device 10 is used to apply a single level of dynamic impact force to an integrated circuit device.

With reference to FIG. 9, an integrated circuit device 500 may be placed within the target area 140 (FIG. 1). A vacuum source (not shown) may be connected to the pneumatic valve assembly 124 and the valve turned on so that vacuum is supplied via the port 128 (FIG. 1) to hold the integrated circuit device 500 in place within the target area 140 throughout the testing process. A predetermined amount of mass (provided, for example, by the weight 400) may then be added to the ram assembly 350. The ram assembly 350 may then be raised such that the tip 450 is located at a height "H" above the top of the integrated circuit device 500. Raising the ram assembly in this manner may be accomplished, for example, manually by having a human user grasp the head portion 382 of the ram assembly 350 and apply an upward force. Thereafter, the user may release the head portion 382, allowing the ram assembly 350 to drop due to the force of gravity until the tip 450 impacts the integrated circuit device 500 being tested.

In order to determine the threshold dynamic impact force that will cause damage to a particular integrated circuit device, the procedure described above may be repeated while the amount of dynamic impact force applied to the device is incremented. One method of incrementing the dynamic impact force is to increment the mass added to the ram assembly 350 over a series of impacts. A process according to this method is illustrated in flow chart form in FIG. 10.

Figure 10:
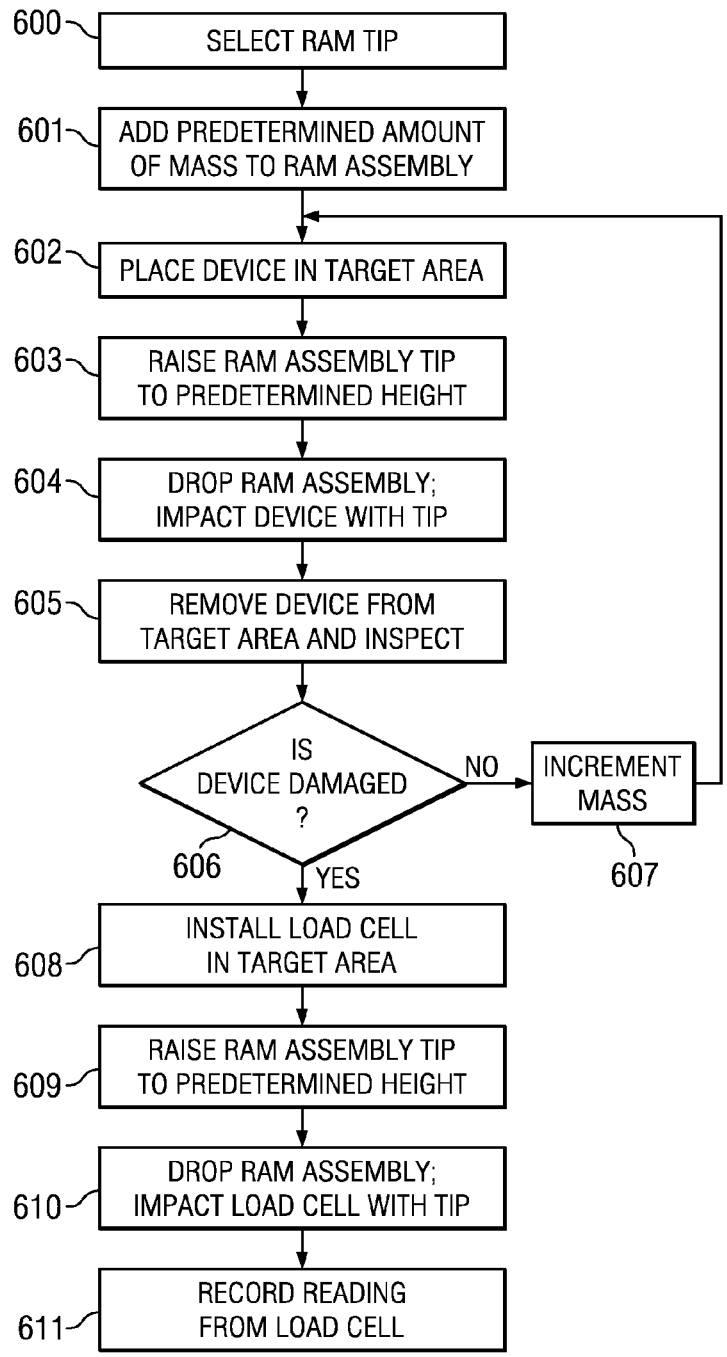
FIG. 10 is a flowchart depicting an exemplary testing process usable in conjunction with the exemplary dynamic impact testing device of FIG. 1.

With reference to FIG. 10, in step 600, an appropriate size and composition ram tip 450 (e.g., FIG. 1) is first selected for impact testing and installed on the threaded stud 398 of the ram assembly 350, FIG. 6.

With further reference to FIG. 10, in step 601, a predetermined amount of mass may be added to the ram assembly 350. This initial amount of mass will typically be selected to be a relatively low amount. Once determined, the desired amount of mass may be added to the ram assembly by selecting the appropriate weight (e.g., the weight 400, FIGS. 7-9) or combination of weights in a manner as previously discussed herein. If, for example, the predetermined amount of mass selected is to be 1.5 grams, then a 0.5 gram weight and a 1 gram weight may be added to the ram assembly.

With continued reference to FIG. 10, in step 602, an integrated circuit device, e.g., the device 500 (FIG. 9), may be placed within the target area 140 (FIG. 1) of the dynamic impact testing device 10. At this point, vacuum may be supplied to the port 128 to assist in holding the integrated circuit device 500 in place within the target area 140, in a manner as previously described herein.

In step 603, the ram assembly 350 may be raised such that the tip 450 is located at a predetermined height "H" (FIG. 9) above the top of the integrated circuit device 500 in a manner as previously described herein.

In step 604, the ram assembly may be released, allowing it to drop due to the force of gravity until the tip 450 impacts the integrated circuit device 500 being tested with a level of dynamic force dictated by a combination of the mass of the ram assembly 350 and the height "H" from which the ram assembly 350 was dropped.

In step 605, after the integrated circuit device 500 has been impacted by the ram assembly tip 450, the integrated circuit device may be removed from the dynamic impact testing device 10, decapsulated and inspected for damage (e.g., silicon die cracks) caused by the impact. Such inspection may, for example, be conducted with the aid of an optical or electron microscope, as desired.

In step 606, a decision is made depending upon whether or not damage is observed during the step 605 inspection. Specifically, if damage is not observed, then the process transfers to step 607 where the amount of mass added to the ram assembly is incremented by a predetermined amount and the process thereafter returns to step 602 wherein the integrated circuit device 500 is placed back into the target area and testing is repeated using the incremented mass amount. This sub-process is repeated until a mass is reached where damage to the integrated circuit device is observed.

Figure 11:
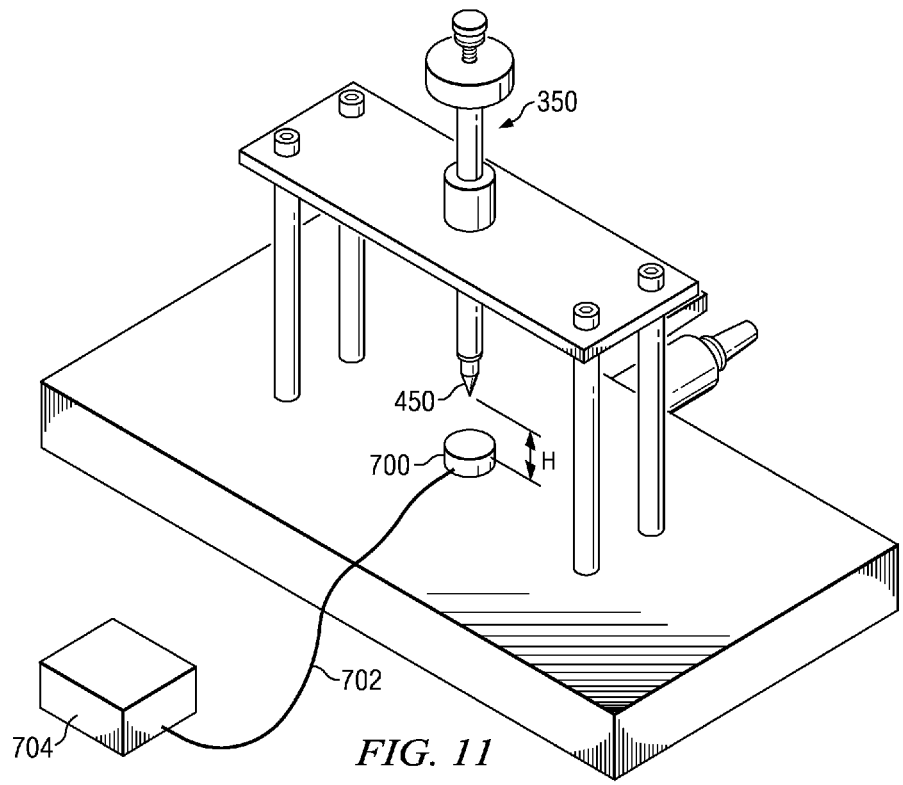
FIG. 11 is a front perspective view of the exemplary dynamic impact testing device of FIG. 1, having a load cell inserted therein.

If, on the other hand, damage is observed in the FIG. 10, block 606 decision step, then the process flow transfers to block 608, wherein a load cell is inserted into the target area 140. The load cell used for this purpose may be any conventional load cell, for example a Futek model #LLB130 Wheatstone Bridge type. FIG. 11 schematically illustrates an exemplary arrangement where a load cell 700 has been inserted into the target area 140 (FIG. 1). The load cell 700 may be connected via a cable 702 to a data collection device 704, in a conventional manner.

Returning to FIG. 10, in step 609, the ram assembly 350 may be raised such that the tip 450 is located at the predetermined height "H" (i.e., the last height "H" used in step 603 when damage was detected) above the top of the load cell 700, as shown in FIG. 11.

In step 610 of FIG. 10, the ram assembly may be released, allowing it to drop due to the force of gravity until the tip 450 impacts the load cell 700 (FIG. 11) positioned within the target area 140 (FIG. 1). Vacuum supplied via the port 128 (FIG. 1) may be used to help hold the load cell 700 in place within the target area 140 while it is being impacted. During impact, data from the load cell 700 may be transmitted, via the cable 702, to the data collection device 704.

Figure 12:
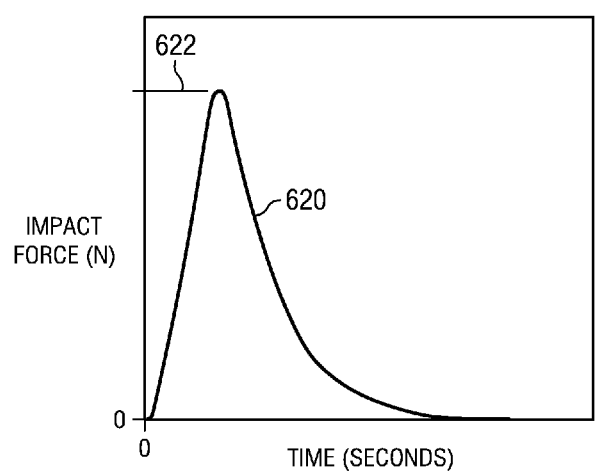
FIG. 12 is a graph illustrating exemplary output from the load cell of FIG. 11.

In step 611 of FIG. 10, the load cell data generated by the impact in step 610 and transmitted to the data collection device 704 (FIG. 11) is analyzed to determine the maximum or peak force developed. FIG. 12 graphically illustrates an exemplary load cell output from the single impact. More specifically, FIG. 11 illustrates a graph in which force (e.g., in Newtons) is measured on the "y" axis and time (e.g., in seconds) is measured on the "x" axis. The plotted line 620 represents an exemplary output from a load cell, showing how the force measured by the load cell varies over time during the impact. In the example of FIG. 12, the force level 622 represents the peak force developed by the impact. Once determined, this peak force level is recorded in association with the integrated circuit device tested and represents the minimum or threshold dynamic impact force that will cause damage to that particular integrated circuit device.

Once the threshold dynamic impact force is known for a particular integrated circuit device, this information may be used to ensure that production machinery used in conjunction with the integrated circuit device does not exceed this threshold force and cause damage.

It is noted that, in the process described above, the dynamic impact force was varied during each iteration of the test by changing the mass applied to the ram assembly 350, while maintaining the ram height constant. As an alternative, the level of dynamic force could be altered by varying the height of the ram assembly before each drop or by a changing a combination of the mass and the ram assembly height.

It is further noted that, in the process described above, the dynamic force is increased during each successive iteration of the test. As an alternative, the initial dynamic force applied could be chosen to be relatively high such that it causes damage to the integrated circuit device. Then, during successive iterations of the test, the dynamic force could be lowered until a point is reached where no damage to the integrated circuit device is detected.

As noted previously, the design of the ram assembly 350 allows actual tips from production machines (e.g., the tip 810 in FIG. 14) to be used in order to more closely model the actual production environment during testing. Accordingly, the testing process described above may readily be conducted for a number of production tips to determine the level of damage caused by each of a variety of tips. In this manner, the dynamic impact testing device 10 may also facilitate the evaluation and selection of different types of tips (e.g., plastic vs. steel) to minimize damage.

Figure 13:
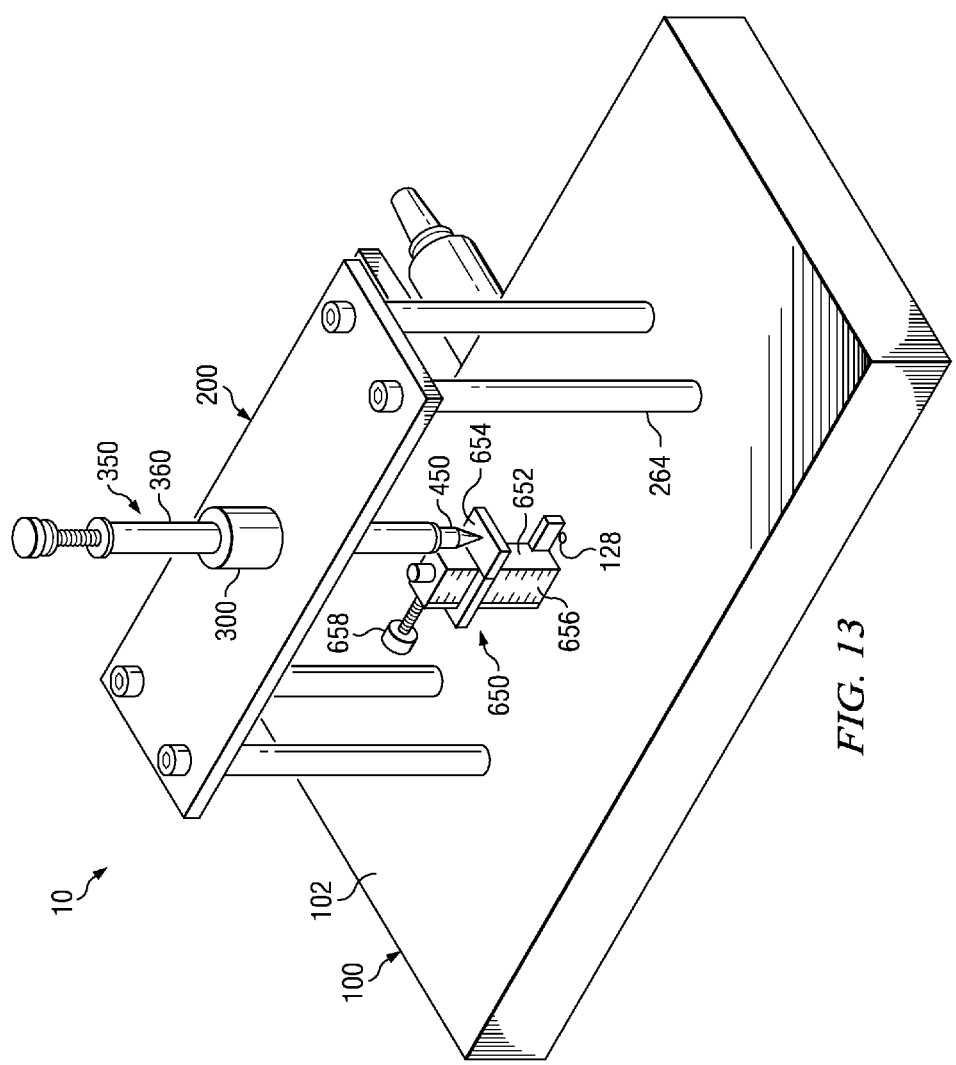
FIG. 13 is a front perspective view of the exemplary dynamic impact testing device of FIG. 1, illustrating an exemplary height gauge optionally usable in association therewith.

FIG. 13 illustrates an alternative and optional embodiment in which a height gauge 650 may be used to set the height of the ram assembly tip 450, for example, in the process block 603 of FIG. 10. With reference to FIG. 13, the height gauge 650 may include a main body portion 652. The main body portion 652 may have a downwardly extending pin (not shown) formed on a lower surface thereof for engaging within the non-threaded hole 138 (FIG. 1) of the dynamic impact testing device base portion 100. In this manner, the height gauge 650 may be temporarily secured in place against the upper surface 102 of the base portion 100. Height gauge 650 may also include a movable ram rest 654 and a scaled ruler 656, as shown. A thumb screw 658 may be threadingly engaged within a portion of the ram rest 654 in order to temporarily hold the ram rest 654 in place relative to the body portion 652.

To use the height gauge 650 to set the height of the ram assembly tip 450, the height gauge 650 may first be placed as shown in FIG. 13 with the ram rest adjusted to the desired position using the scaled ruler 656. The ram assembly 350 may then be positioned as shown in FIG. 13 with the ram assembly tip 450 resting on the ram rest 654. The ram shaft 360 may then be marked relative to the ram guide 300 and the height gauge removed from the dynamic impact testing device 10. Thereafter, positioning the ram assembly 350 so that the mark aligns with the top of the ram guide 300 will place the ram assembly 350 at the desired height.

Figure 13A:
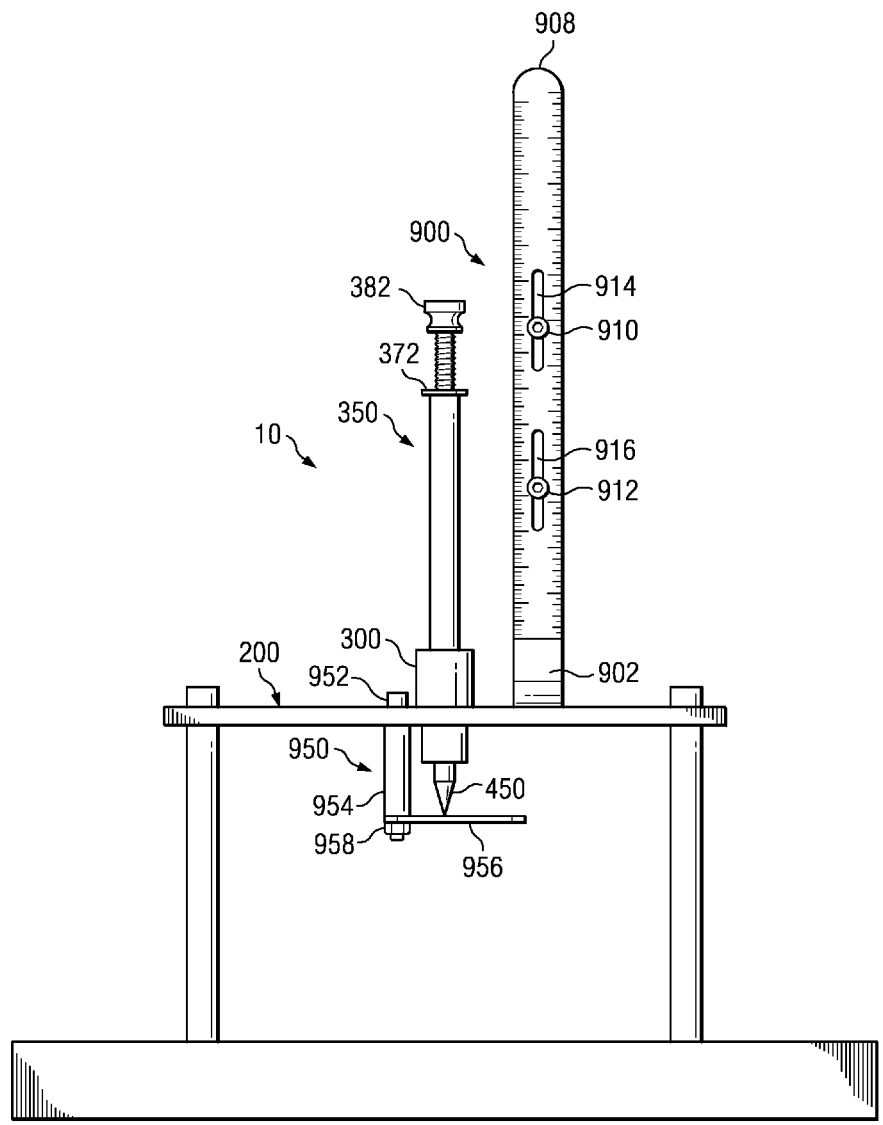
FIG. 13A is a front elevation view of the exemplary dynamic impact testing device of FIG. 1, illustrating an alternative exemplary height gauge mechanism optionally usable in association therewith.
Figure 13B:
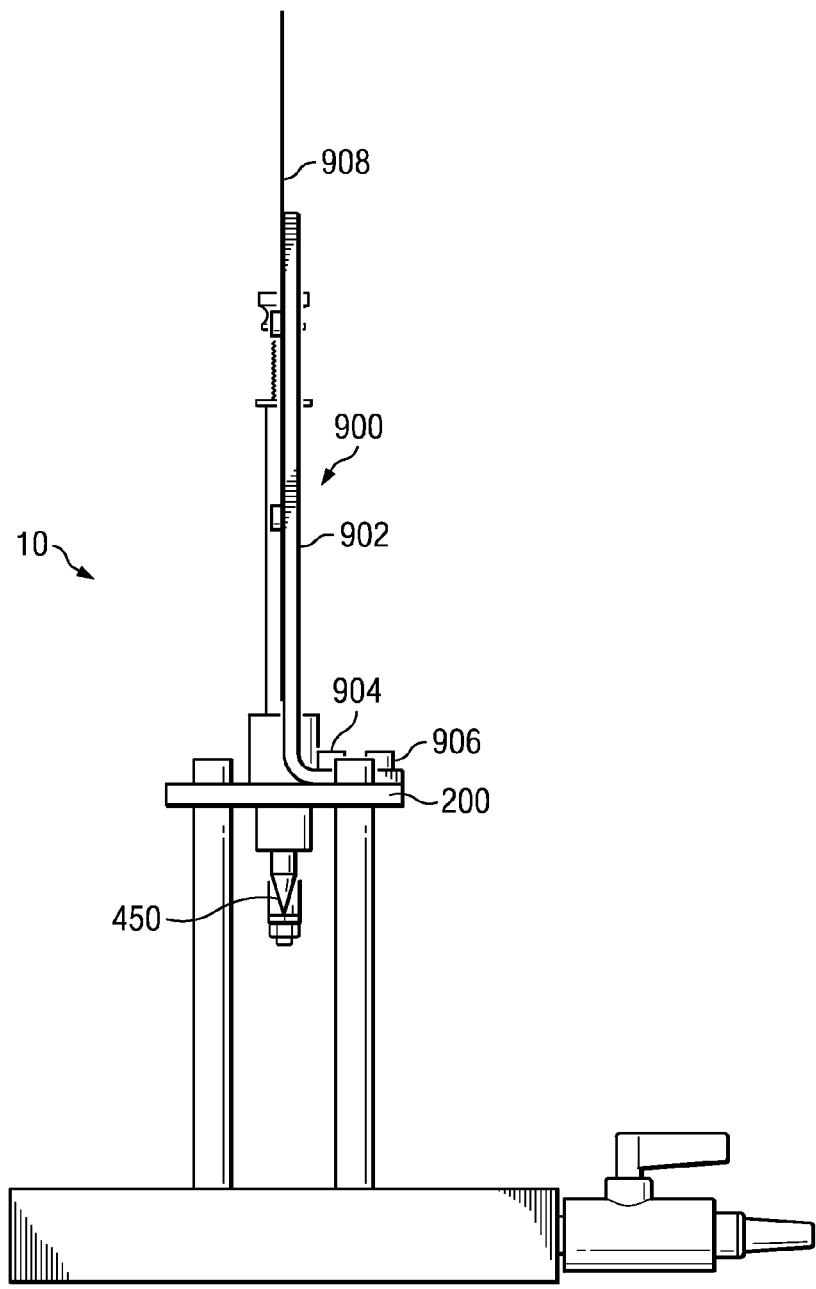
FIG. 13B is a side elevation view of the alternative exemplary height gauge mechanism of FIG. 13A.

FIGS. 13A and 13B illustrate a further alternative and optional arrangement for setting the height of the ram assembly tip 450, for example, in the process block 603 of FIG. 10. With reference to FIG. 13A, a height gauge assembly 900 may include an L-shaped bracket 902 having its bottom flange secured to the top plate 200 of the dynamic impact testing device 10 via a pair of screws 904, 906. A scaled ruler 908 may be secured to the upright portion of L-shaped bracket 902 via a pair of screws 910, 912 which pass through a pair of slots 914, 916, respectively, formed in the scaled ruler 908. The scaled ruler may be adjusted, for example, such that the ram assembly shoulder portion 372 is adjacent the "zero" mark when the ram assembly tip 450 is resting in the fully down position against an integrated circuit device to be tested. As can be appreciated, the slots 914, 916 readily facilitate this adjustment. The scaled ruler 908 may, for example, be formed from stainless steel. To use the height gauge assembly 900 to set the height of the ram assembly tip 450, the ram assembly shoulder portion 372 may be positioned at the desired marking on scaled ruler 908.

With further reference to FIGS. 13A and 13B, a ram stop assembly 950 may optionally be provided, as shown. Ram stop assembly 950 may include a threaded screw 952 that passes through a non-threaded hole in the top plate 200, a non-threaded spacer 954, and a non-threaded hole in a plate member 956 before threadingly engaging with a lock nut 958. As can be appreciated, this arrangement allows the plate member 956 to be pivoted about the axis of the threaded screw 952. When the plate member 956 is rotated to the position shown in FIGS. 13A and 13B, it holds the ram assembly 350 in a raised position such that various operations can conveniently be accomplished (e.g., adding weights to the ram assembly or placing an integrated circuit device into the target area 140, FIG. 1). When the ram assembly is to be dropped for a test, the plate member 956 can simply be pivoted out of the way.

As discussed above, the dynamic impact testing device 10 may be used to determine the threshold dynamic impact force for a particular integrated circuit device, i.e, the dynamic impact force where damage will begin to occur. Discussed below is a method of determining the maximum dynamic impact forces that can be generated by a piece of production machinery under various machine settings. This information, in association with the determined threshold dynamic impact force necessary to cause damage to an integrated circuit device may be used to determine whether a particular production machine is capable of causing damage to the integrated circuit device in question.

As discussed previously, FIG. 14 schematically illustrates a production machine 800 which may be used in conjunction with the manufacture of an integrated circuit device 500. Specifically, production machine 800 may include a work platform 802 for supporting the integrated circuit device 500, as shown. Work platform 802 may, for example, be a portion of a conventional rotary table mechanism. A plunger 804 may be reciprocally movable in the upward 806 and downward 808 directions relative to the work platform 802. A tip 810 may be attached to the plunger 804.

As also discussed previously, it is possible for the initial contact, or impact, between the tip 810 and the integrated circuit device 500 to cause damage to the integrated circuit device. As noted previously, such damage usually takes the form of small internal silicon die cracks which may later enlarge during heat cycling (e.g., soldering operations) and cause failure of the integrated circuit device. Similar impact damage can also occur during the pick and place machine placing operation.

Figure 15:
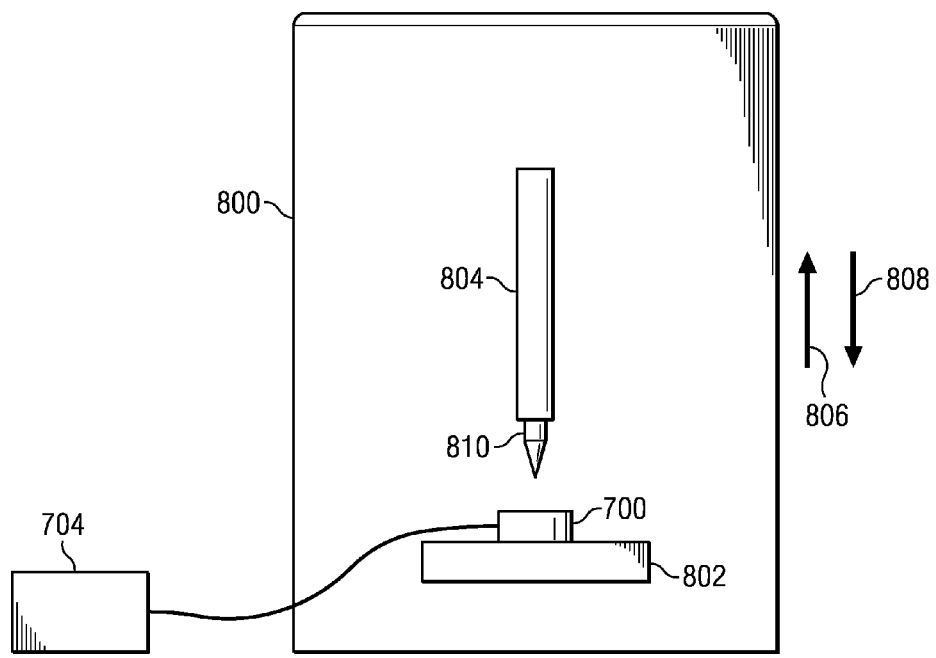
FIG. 15 is a schematic front elevation view of the portion of an exemplary production machine of FIG. 14, having a load cell inserted therein, in place of the integrated circuit device.

In FIG. 15, a load cell 700 has been installed on the work platform 802 in place of the integrated circuit device 500. The load cell 700 may be connected via a cable 702 to a data collection device 704, in a conventional manner. The load cell 700 may be the same load cell, or type of load cell, used in conjunction with the dynamic impact testing device 10, i.e., the load cell 700 shown in FIG. 11. In order to measure the dynamic impact force that the machine 800 can generate, the machine 800 in FIG. 15 may be cycled through its operation, allowing the tip 810 to impact the load cell 700. During impact, data from the load cell 700 may be transmitted, via the cable 702, to the data collection device 704 and the maximum or peak dynamic force generated by the machine may be recorded.

As discussed previously, various machine parameters affect the likelihood of damage being inflicted. One such parameter is the speed at which the plunger 804 moves in the downward direction 806. Another is the "overdrive" setting of the plunger, i.e., the distance the plunger 804 can travel beyond initial contact with the integrated circuit device. Accordingly, the force measurement process described above may be repeated for each of the various machine settings and parameters to determine the maximum force generated for each setting and/or parameter.

Once the machine forces have been measured, in a manner as described above, these force measurements may be used in conjunction with the integrated circuit device measurements to ensure that the machine is adjusted properly to avoid damage to a particular integrated circuit device.

The foregoing description of specific embodiments of the present invention has been presented for purposes of illustration and description. They are not intended to be exhaustive or to limit the invention to the precise forms disclosed, and many modifications and variations are possible in light of the above teaching. The embodiments of the invention described herein were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method of determining the level of dynamic force required to cause damage to an electronic device, said method comprising:
   selecting a tip member from a plurality of different types of tip members;
   inserting said selected tip member in a vertically movable ram assembly;
   adjusting the mass of said vertically movable ram assembly with selected tip member to a predetermined mass;
   placing an electronic device beneath said ram assembly with selected tip member;
   positioning said ram assembly with selected tip member a predetermined height above said electronic device;
   dropping said ram assembly with selected tip member and having said predetermined mass from said predetermined height, thereby causing said ram assembly with selected tip member to impact said electronic device;
   inspecting said electronic device for damage;
   changing at least one of said predetermined mass and said predetermined height and thereafter repeating said impacting and said inspecting until a threshold mass and height is determined where damage occurs to said electronic device;
   placing a load cell beneath said ram assembly with selected tip member, after said inspecting;
   dropping said ram assembly with selected tip member and having said threshold mass from said threshold height, thereby causing said ram assembly to impact said load cell and cause said load cell to generate data output therefrom; and
   recording the data output from said load cell.

2. The method of claim 1 and further wherein: said changing at least one of said predetermined mass and said predetermined height comprises incrementing said predetermined mass.

3. The method of claim 1 and further wherein: said changing at least one of said predetermined mass and said predetermined height comprises decreasing said predetermined mass.

4. The method of claim 1 and further comprising: using vacuum to maintain said electronic device in position beneath said vertically movable ram assembly with selected tip member.

5. The method of claim 1 and further comprising: using vacuum to maintain said load cell in position beneath said vertically movable ram assembly with selected tip member.

6. The method of claim 1 and further wherein: said positioning said vertically movable ram assembly with selected tip member a predetermined height above said electronic device comprises using a height gauge to set said predetermined height.

7. The method of claim 1 and further wherein: said recording the high-speed data output from said load cell comprises recording the peak force detected by said load cell.

8. The method of claim 1 and further wherein: said inspecting said electronic device for damage comprises decapsulating and inspecting said electronic device with one of an optical microscope or an electron microscope.

9. A method comprising:
    determining a pick and place (PNP) machine to model;
    placing an electronic device beneath a ram assembly of a dynamic impact testing device;
    inserting a tip member, selected from a plurality of different types of tip members, that is useable in the modeled PNP machine;
    impacting said electronic device with said ram assembly with selected tip member to determine a threshold level of dynamic impact force that will cause damage to said electronic device;
    placing a load cell beneath said ram assembly with selected tip member, after said impacting said electronic device;
    using said ram assembly with selected tip member to impact said load cell with said threshold level of dynamic impact force, thereby causing said load cell to generate a first data output therefrom.

10. The method of claim 9 and further comprising: placing said load cell in said modeled PNP machine; impacting said load cell with a portion of said modeled PNP machine, thereby causing said load cell to generate a second data output therefrom; and comparing said first data output and said second data output to determine whether said modeled PNP machine will cause damage to said electronic device.

11. The method of claim 9 and further wherein: said tip member is a vacuum tip member.

12. The method of claim 9 and further comprising: using vacuum to maintain said electronic device in position beneath said ram assembly.

13. The method of claim 9 and further comprising: using vacuum to maintain said load cell in position beneath said ram assembly.

14. The method of claim 10 and further wherein: said comparing said first data output and said second data output comprises comparing the peak force levels detected by said load cell.

* * * * *